(12) United States Patent
Kim et al.

(10) Patent No.: US 9,968,868 B2
(45) Date of Patent: May 15, 2018

(54) PORE WATER EXTRACTION KIT OF SEABED SEDIMENT

(71) Applicant: KOREA INSTITUTE OF GEOSCIENCE AND MINERAL RESOURCES, Daejeon (KR)

(72) Inventors: Yuri Kim, Daejeon (KR); Jong-Hwa Chun, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 87 days.

(21) Appl. No.: 14/934,239

(22) Filed: Nov. 6, 2015

(65) Prior Publication Data

US 2017/0007945 A1     Jan. 12, 2017

(30) Foreign Application Priority Data

Jul. 9, 2015    (KR) ........................ 10-2015-0097695

(51) Int. Cl.
| | |
|---|---|
| *E21B 49/00* | (2006.01) |
| *C02F 1/38* | (2006.01) |
| *B01D 21/26* | (2006.01) |
| *B01L 3/00* | (2006.01) |
| *G01N 1/40* | (2006.01) |
| *A61M 39/14* | (2006.01) |
| *C02F 1/44* | (2006.01) |
| *A61M 5/162* | (2006.01) |
| *G01N 33/18* | (2006.01) |

(52) U.S. Cl.
CPC .......... *B01D 21/262* (2013.01); *B01L 3/5021* (2013.01); *E21B 49/00* (2013.01); *G01N 1/4077* (2013.01); *A61M 5/162* (2013.01); *A61M 39/14* (2013.01); *B01L 2200/026* (2013.01); *B01L 2200/0621* (2013.01); *B01L 2300/044* (2013.01); *B01L 2300/0672* (2013.01); *B01L 2300/0681* (2013.01); *B01L 2300/0832* (2013.01); *B01L 2300/0858* (2013.01); *B01L 2300/123* (2013.01); *B01L 2400/0478* (2013.01); *C02F 1/38* (2013.01); *C02F 1/44* (2013.01); *G01N 33/18* (2013.01); *G01N 2001/4088* (2013.01)

(58) Field of Classification Search
None
See application file for complete search history.

(56) References Cited

U.S. PATENT DOCUMENTS

| | | | | |
|---|---|---|---|---|
| 5,122,116 A | * | 6/1992 | Kriesel | ................. A61M 5/152 604/122 |
| 6,786,244 B1 | * | 9/2004 | Jones | .................... A61M 39/14 141/18 |
| 2014/0352845 A1 | * | 12/2014 | Lev | ....................... A61J 1/2089 141/329 |

FOREIGN PATENT DOCUMENTS

KR    20-1999-0025095 A    7/1999

* cited by examiner

*Primary Examiner* — Neil N Turk
(74) *Attorney, Agent, or Firm* — Hauptman Ham, LLP

(57) ABSTRACT

Provided is a pore water extraction kit for extracting pore water in a seabed sediment. More specifically, provided is a pore water extraction kit of a seabed sediment for more easily extracting pore water separated from a sediment through a centrifugal separator tube.

7 Claims, 5 Drawing Sheets

[Figure 5]
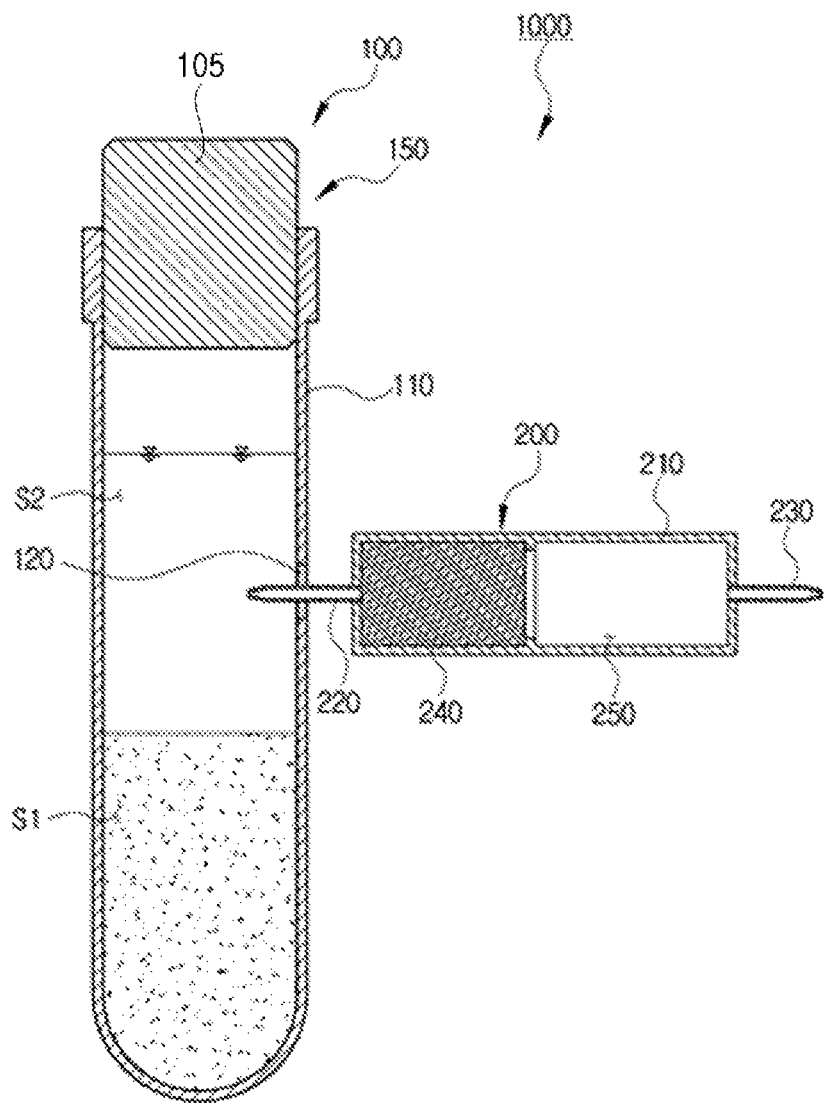

[Figure 6]
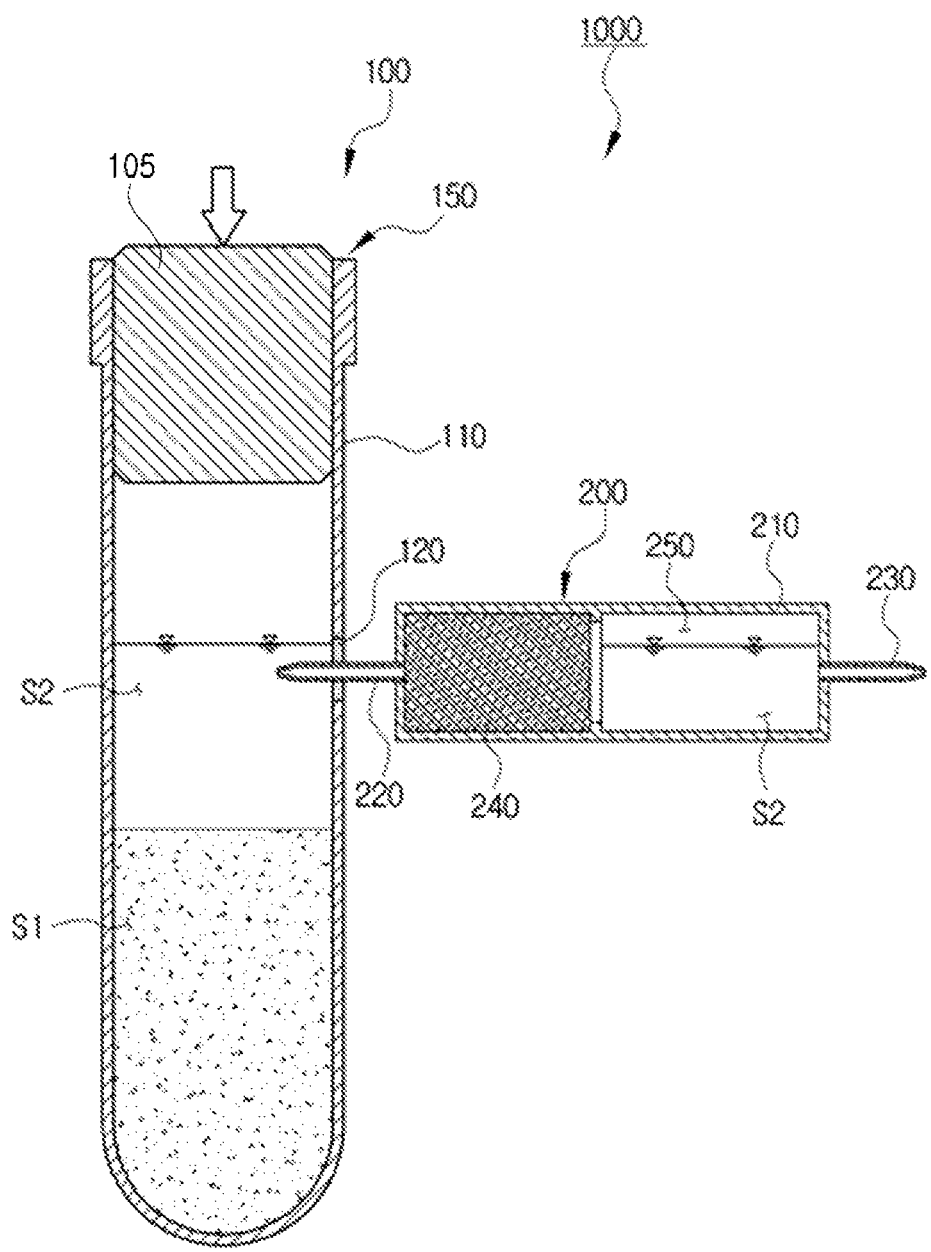

PORE WATER EXTRACTION KIT OF SEABED SEDIMENT

CROSS-REFERENCE TO RELATED APPLICATIONS

This application claims priority under 35 U.S.C. § 119 to Korean Patent Application No. 10-2015-0097695, filed on Jul. 9, 2015, in the Korean Intellectual Property Office, the disclosure of which is incorporated herein by reference in its entirety.

TECHNICAL FIELD

The following disclosure relates to a pore water extraction kit for extracting pore water in a seabed sediment. More particularly, the following disclosure relates to a pore water extraction kit of a seabed sediment for more easily extracting pore water separated from a sediment through a centrifugal separator tube.

BACKGROUND

Recently, an interest in exploration and development of a non-conventional energy resource such as gas hydrate, shale gas, or the like, as well as exploration of a conventional energy resource such as petroleum or gas has been gradually increased, and an exploration area has also been gradually enlarged from a continental shelf to the deep sea.

In order to explore and develop the conventional and non-conventional energy resources, ocean exploration has been performed using an exploration vessel. As the ocean exploration using the exploration vessel, there are a geophysical survey of figuring out a structure and a development process of a seabed sedimentary layer using a seismic survey equipment, or the like, and an ocean geological survey of directly collecting a pillar seabed sediment using a drilling machine.

Various analyses such as a grain size analysis of the sediment, a content analysis of dissolved gas, a geochemistry analysis, a micropalaeontological analysis, and the like, may be performed on a pillar seabed sediment sample obtained through the ocean geological survey, and this may be utilized in fields such as an ocean environment, a stratigraphic analysis, and the like, of an exploration area to figure out a generation mechanism, the origin, blessed possibility, and the like, of the conventional and non-conventional energy resources.

However, in the ocean geological survey performed in the ocean, many ocean samples should be obtained within a relatively short exploration period, and an analysis on the obtained samples should be rapidly performed on the ship in order to decrease pollution of the samples as much as possible and obtain an accurate analysis result.

Particularly, results obtained by directly extracting and analyzing pore water present between particles of the seabed sediment on the ship are utilized as important data in confirming whether or not gas hydrate is blessed or figuring out a section in which a sulfate reducing reaction is generated within the seabed sedimentary layer.

In the related art, in order to extract the pore water from the seabed sediment, a method of putting the pillar seabed sediment in a centrifugal separator tube on the ship to centrifuge the pillar seabed sediment, putting the pore water extracted in the centrifugal separator tube in a primary sample container using a disposable pipette, filtering the pore water put in the primary sample container using a syringe to which a filter is connected, and finally putting the filtered pore water in a secondary sample container has been used.

However, in the process of extracting the pore water described above, the number of used experimental tools is many, such that the process of extracting the pore water is very complicated. Therefore, it is very likely that a pore water sample will be polluted. In addition, a long time is required for extracting the pore water, such that the next work is delayed.

SUMMARY

An embodiment of the present invention is directed to providing a pore water extraction kit of a seabed sediment capable of extracting pore water by a needle of an extractor through an elastic membrane formed on a pore water separating region of a centrifugal separator tube.

Another embodiment of the present invention is directed to providing a pore water extraction kit of a seabed sediment capable of supplying pore water to an extractor by applying a pressing apparatus to a cap of a centrifugal separator tube and pressing the pressing apparatus in a state in which a needle of the extractor is injected into the centrifugal separator tube.

Still another embodiment of the present invention is directed to providing a pore water extraction kit of a seabed sediment capable of allowing pore water to be filtered simultaneously with being supplied to an extractor by including a filter disposed at an introduction stage of the extractor.

In one general aspect, a pore water extraction kit of a seabed sediment includes: a centrifugal separator tube including a sample accommodating space formed therein so as to store a sample, an extraction hole formed in an outer surface thereof in order to extract pore water separated from the sample, and an elastic membrane sealing the extraction hole; and an extractor including a pore water accommodating space formed therein so as to accommodate the pore water and a needle formed at one end thereof so as to penetrate through the elastic membrane to allow the sample accommodating space and the pore water accommodating space to be in communication with each other.

A plurality of extraction holes may be disposed to be spaced apart from each other in a length direction of the centrifugal separator tube.

The extraction hole may be formed at a position higher than a boundary between the sediment and the pore water within the centrifugal separator tube.

The centrifugal separator tube may be configured so that an upper side thereof is opened and is openable and closable by a cap, and the cap may be provided with a pressing apparatus so as to apply pressure to the sample accommodating space.

The extractor may include a filter disposed at an introduction side of the pore water accommodating space and filtering the pore water introduced into the pore water accommodating space.

BRIEF DESCRIPTION OF THE DRAWINGS

FIG. 5 is a view illustrating a process (needle injection) of the pore water extraction kit according to an exemplary embodiment of the present invention.

FIG. 6 is a view illustrating a process (pore water extraction) of the pore water extraction kit according to an exemplary embodiment of the present invention.

DETAILED DESCRIPTION OF MAIN ELEMENTS

Figure 1:
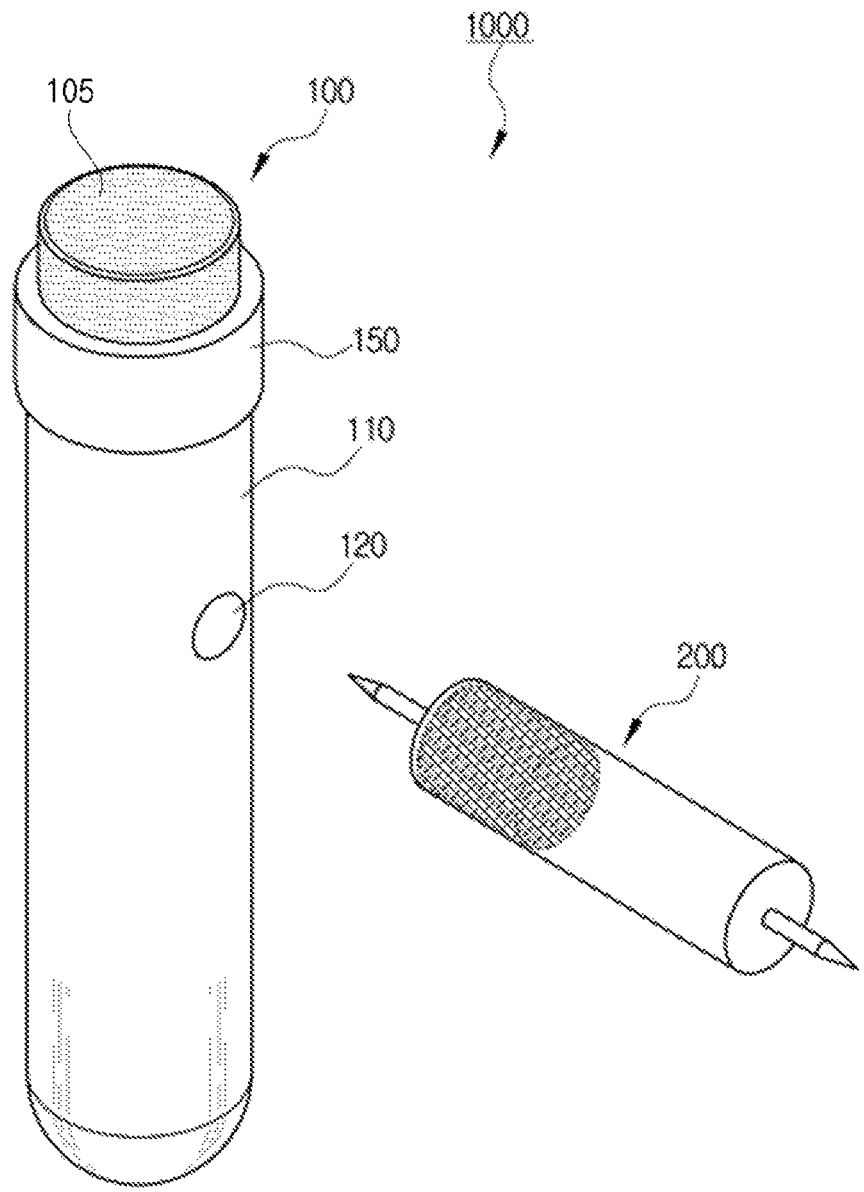
FIG. 1 is an entire perspective view of a pore water extraction kit according to an exemplary embodiment of the present invention.

1000: extraction kit
100: centrifugal separator tube
110: tube body
120: elastic membrane
150: cap
200: extractor
210: extractor body
220: needle for introduction
230: needle for discharging
240: filter
250: pore water accommodating space

DETAILED DESCRIPTION OF EMBODIMENTS

Hereinafter, an exemplary embodiment of the present invention will be described in detail with reference to the accompanying drawings.

In FIG. 1, an entire perspective view of a pore water extraction kit 1000 (hereinafter, referred to as an "extraction kit") of a seabed sediment according to an exemplary embodiment of the present invention is illustrated. As illustrated in FIG. 1, the extraction kit 1000 according to an exemplary embodiment of the present invention is configured to include a centrifugal separator tube 100 accommodating a sample therein and separating a sediment and pore water from each other through a centrifugal separator and an extractor 200 extracting the pore water separated through the centrifugal separator tube 100.

Figure 2:
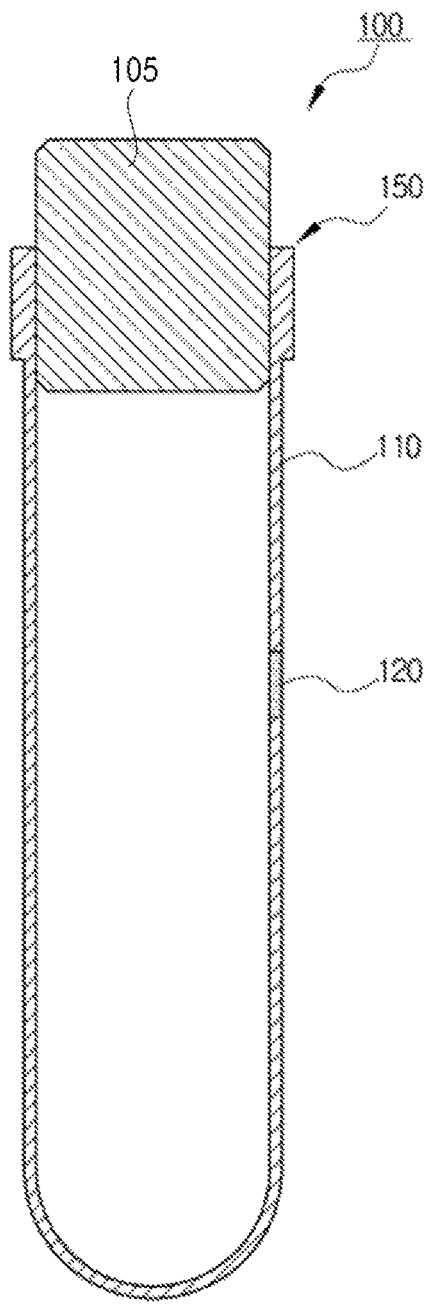
FIG. 2 is a cross-sectional view of a centrifugal separator tube according to an exemplary embodiment of the present invention.

In FIG. 2, a cross-sectional view of a centrifugal separator tube 100 according to an exemplary embodiment of the present invention is illustrated. As illustrated in FIG. 2, the centrifugal separator tube 100 is configured to include a tube body 110 having a sample accommodating space 101 formed therein, a cap 150 opening or closing an upper side of the tube body 110 of which the upper side is opened, and an elastic membrane 120 sealing an extraction hole (not illustrated) penetrated and formed in the tube body 110. The extraction hole is configured in order to extract the pore water separated in the sample accommodating space 101 to the outside, and since the extraction hole is sealed through the elastic membrane 120, the extraction hole may be configured to easily extract the pore water by injecting the elastic membrane 120 thereinto through a component such as a needle of a syringe.

Here, it is preferable that the elastic membrane 120 is formed at a position higher than a boundary on which the sediment and the pore water are separated from each other. In addition, a plurality of extraction holes are formed in a vertical length direction, such that the pore water may be extracted from an extraction hole corresponding to the boundary between the sediment and the pore water.

In addition, the cap 150 may be provided with a pressing apparatus 105 applying pressure to the sample accommodating space 101 to assist in the extraction of the pore water accommodated in the sample accommodating space 101.

Figure 3:
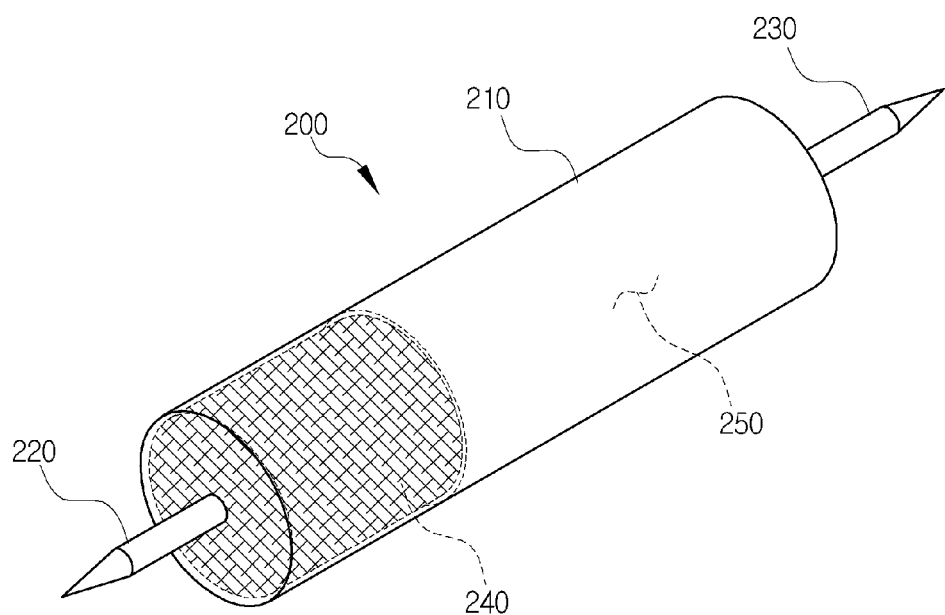
FIG. 3 is a perspective view of an extractor according to an exemplary embodiment of the present invention.
Figure 4:
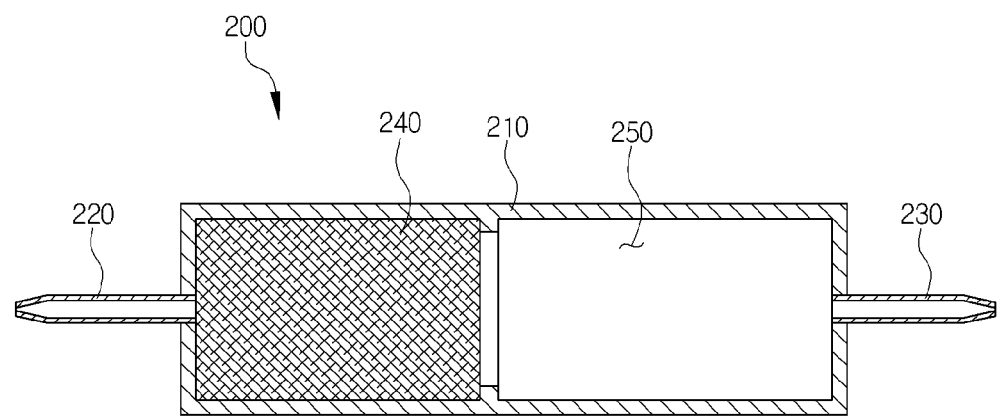
FIG. 4 is a cross-sectional view of the extractor according to an exemplary embodiment of the present invention.

In FIG. 3, a perspective view of an extractor 200 according to an exemplary embodiment of the present invention is illustrated, and in FIG. 4, a cross-sectional view of the extractor 200 according to an exemplary embodiment of the present invention is illustrated. As illustrated in FIGS. 3 and 4, the extractor 200 includes an extractor body 210 in which a pore water accommodating space 250 storing the extracted pore water therein is formed. A needle 220 for introduction of the pore water is formed at one side of the extractor body 210, and a needle 230 for discharging of the pore water is formed at the other side of the extractor body 210. Therefore, when the needle 220 for introduction of the pore water is injected into the elastic membrane 120 of the tube body 110, the sample accommodating space 101 and the pore water accommodating space 250 are in communication with each other, such that the pore water accommodated in the sample accommodating space 101 may be extracted to the pore water accommodating space 250.

Here, the extractor body 210 includes a filter 240 so that the extracted pore water is accommodated in the pore water accommodating space 250 in a state in which it is filtered. The filter 240 may be a general mesh filter for filtering the pore water, and may be disposed at a pore water introduction side in the pore water accommodating space 250.

Hereinafter, an operation of the pore water extraction kit according to an exemplary embodiment of the present invention configured as described above will be described with reference to the accompanying drawings.

In FIG. 5, a view illustrating a process of the pore water extraction kit at the time of injecting the needle is illustrated, and in FIG. 6, a view illustrating a process of the pore water extraction kit at the time of extracting the pore water is illustrated.

As illustrated in FIG. 5, a sediment S1 may be positioned at a lower side of the sample accommodating space 101, and pore water S2 separated from the sediment S1 through the centrifugal separate tube 100 may be positioned at an upper side of the sample accommodating space 101. In this state, when the needle 220 of the extractor 200 is injected through the elastic membrane 120, an extraction preparation state of the pore water is completed.

Next, as illustrated in FIG. 6, when the pressing apparatus 105 of the cap 150 is pressed downward as illustrated in FIG. 6, pressure of the sample accommodating space 101 rises, such that the pore water S2 of the sample accommodating space 101 is introduced into the pore water accommodating space 210 of the extractor 200 through the needle 220. Here, the pore water S2 first passes through the filter 240, such that it is stored in the pore water accommodating space 210 in a state in which it is filtered and is used in the next experiment.

In the pore water extraction kit of a seabed sediment according to an exemplary embodiment of the present invention having the configuration as described above, extraction and filtering for the pore water separated from the sediment through the centrifugal separator tube may be performed at a time through the extractor and be collected in a sample container.

The cap of the centrifugal separator tube is provided with a button type pressing apparatus 105 that may apply pressure, such that the pressure is applied to the pore water within the centrifugal separator tube by a simple operation, thereby making it possible to extract the pore water through the extractor.

The elastic membrane through which the pore water may be extracted is formed in the centrifugal separator tube, and the needle is injected into the elastic membrane, thereby making it possible to easily extract the pore water. Therefore, the pore water separated from the sediment in the centrifugal separator tube may be extracted in a relatively rapid time.

In the case in which the pore water in the centrifugal separator tube is extracted by an existing method, it is very likely that the sample will be polluted. However, since the pore water extracted in the centrifugal separator tube may be directly filtered through the filter, the pollution of the pore water sample may be minimized.

The present invention should not be construed to being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall in the scope of the present invention.

What is claimed is:

1. A pore water extraction kit of a seabed sediment, comprising:
    a centrifugal separator tube including a sample accommodating space formed therein so as to store a sample, an extraction hole formed in an outer surface thereof in order to extract pore water separated from the sample, and an elastic membrane sealing the extraction hole;
    an extractor including an enclosed body that includes opposite facing sidewalls, wherein a pore water accommodating space provided between the sidewalls of the body so as to accommodate the pore water and a needle is attached on one sidewall so as to penetrate through the elastic membrane to allow the sample accommodating space and the pore water accommodating space to be in communication with each other, the extractor further including a needle for discharging, wherein the needle for discharging is provided on an opposite sidewall of the extractor from the needle to penetrate through the elastic membrane; and
    a cap, wherein the centrifugal separator tube has an opening in an upper side thereof and is openable and closable by the cap, and the cap is provided with a compressible button fitted to an inner diameter of the opening in the upper side of the centrifugal separator tube so as to apply pressure to the sample accommodating space for causing pore water to be communicated to the extractor.

2. The pore water extraction kit of a seabed sediment of claim 1, wherein a plurality of extraction holes are disposed to be spaced apart from each other in a length direction of the centrifugal separator tube.

3. The pore water extraction kit of a seabed sediment of claim 1, wherein the extractor includes a filter disposed at an introduction side of the pore water accommodating space and configured to filter the pore water introduced into the pore water accommodating space from the sample accommodating space.

4. A pore water extraction kit of a seabed sediment, comprising:
    a centrifugal separator tube having a sample accommodating space formed therein for storing a sample, an extraction hole formed in an outer surface thereof for extracting pore water separated from the sample, an elastic membrane sealing the extraction hole, and a cap, wherein the centrifugal separator tube has an open upper side for communicating the sample accommodating space with the exterior of the tube, the cap is movable to close the open upper side of the centrifugal separator tube and comprises a compressible button for applying pressure to the sample accommodating space, wherein the compressible button is fitted to an inner diameter of the open upper side of the centrifugal separator tube; and
    an extractor including an enclosed body that includes opposite facing sidewalls, wherein a pore water accommodating space is provided between the sidewalls of the body so as to accommodate the pore water and a needle is attached on one sidewall and configured to penetrate through the elastic membrane to allow the sample accommodating space and the pore water accommodating space to be in communication with each other.

5. The pore water extraction kit of a seabed sediment of claim 4, wherein the extractor further comprises:
    a needle for discharging provided on an opposite sidewall of the extractor from the needle.

6. The pore water extraction kit of a seabed sediment of claim 4, wherein the centrifugal separator tube has a plurality of extraction holes formed therein and disposed to be spaced apart from each other in a length direction of the centrifugal separator tube.

7. The pore water extraction kit of a seabed sediment of claim 4, wherein the extractor includes a filter disposed at an introduction side of the pore water accommodating space and filtering the pore water introduced into the pore water accommodating space.

* * * * *